United States Patent [19]

Hartman et al.

[11] Patent Number: 4,670,443
[45] Date of Patent: Jun. 2, 1987

[54] BENZO(F)ISOQUINOLINE COMPOUNDS USEFUL AS CALCIUM ENTRY BLOCKERS

[75] Inventors: George D. Hartman, Lansdale; Brian T. Phillips, Telford, both of Pa.

[73] Assignee: Merck & Co., Inc., Rahway, N.J.

[21] Appl. No.: 750,953

[22] Filed: Jul. 2, 1985

[51] Int. Cl.$^4$ .................... A61K 31/47; C07D 221/10
[52] U.S. Cl. .................................. 514/290; 546/101; 546/322; 568/425; 568/437; 568/592; 568/812
[58] Field of Search ................. 546/101; 514/290

[56] References Cited

U.S. PATENT DOCUMENTS

| 3,905,970 | 9/1975 | Bossert et al. | 544/82 |
| 3,923,818 | 12/1975 | Bossert et al. | 546/321 |
| 4,044,141 | 8/1977 | Bossert et al. | 514/150 |
| 4,237,137 | 12/1980 | Tacke et al. | 546/14 X |
| 4,285,955 | 8/1981 | Wehinger et al. | 546/322 X |
| 4,532,237 | 7/1985 | Hartman et al. | 514/226 |
| 4,591,587 | 5/1986 | Remy | 514/222 |
| 4,593,033 | 6/1986 | Hartman et al. | 514/290 |
| 4,605,660 | 8/1986 | Remy | 514/290 |

OTHER PUBLICATIONS

Weller, et al., J. Org. Chem., vol. 48, pp. 3061–3067 (1983).
Goldmann, Angew. Chem. Int. Ed. Engl., vol. 20, No. 9, pp. 779–780 (1981).
Hartman, et al., J. Org. Chem., vol. 50(14), pp. 2423–2431 (07/12/85).

Primary Examiner—Donald G. Daus
Assistant Examiner—Diana G. Rivers
Attorney, Agent, or Firm—Alice O. Robertson; Michael C. Sudol, Jr.

[57] ABSTRACT

Benzo(f)isoquinoline compounds, particularly, penta- and tetrahydrobenzo(f)isoquinoline dicarboxylic acid compounds, their preparation and their use as calcium entry blockers are disclosed.

8 Claims, No Drawings

BENZO(F)ISOQUINOLINE COMPOUNDS USEFUL AS CALCIUM ENTRY BLOCKERS

DESCRIPTION OF THE INVENTION

The present invention is directed to benzo(f)isoquinoline compounds, more specifically to compounds represented by the formulas

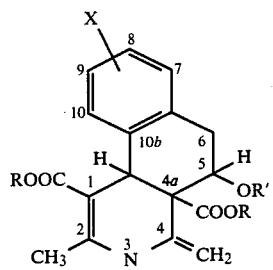
(IA)

and

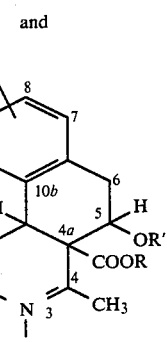
(IB)

In this and succeeding formulas, X is hydrogen, lower alkyl, lower alkoxy, halogen, trifluoromethyl or nitro; R is lower alkyl and R' is lower alkyl.

By "lower alkyl" is meant an alkyl group having from 1 to 6 carbon atoms, which may be straight chain or branched. Representative groups include methyl, isopropyl, tertiary-butyl, isoamyl, n-hexyl, 2,2-dimethylpropyl, ethyl, n-butyl and the like.

By "lower alkoxy" is meant a straight or branched chain alkoxy group having from 1 to 6 carbon atoms. Representative groups include methoxy, ethoxy, isopropoxy, n-propoxy, t-butoxy, n-butoxy, n-hexyloxy, n-pentyloxy, 3-methylbutoxy and the like.

By "halogen" is meant chlorine, bromine or flourine.

The compounds of the present invention are tautomeric mixtures which are also capable of existing in stereoisomeric forms. Representative isomeric forms may be seen in structural formulas IA', IA", IB' and IB":

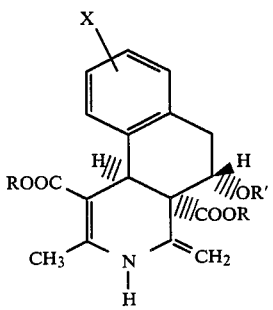
(IA')

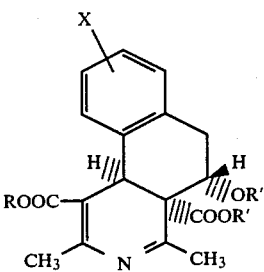
(IB')

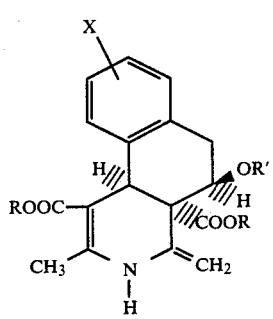
(IA")

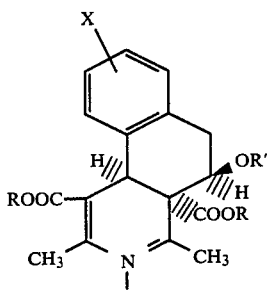
(IB")

The present invention embraces compounds represented not only by the foregoing formulas but all isomeric forms.

The products of the present invention are crystalline solids, soluble in most nonpolar organic solvents. A single isomeric form of the product is not readily obtainable as a crystalline solid. However, a crystalline product may be obtained which has been found by NMR determinations to be a mixture of tautomers present in a particular ratio. The products exhibit pharmacological properties adaptable for therapeutic application. The property of inhibiting calcium induced contraction of tracheal smooth muscle or vascular tissue render the products adaptable for therapeutic application as cardiovascular agents.

The compounds of the present invention may be prepared by the cyclization of a dihydropyridine compound represented by the formula

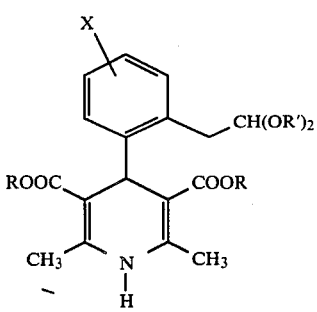 (II)

in the presence of an acid to obtain the cyclized products IA and IB as a tautomeric mixture. The product mixture may be recovered from the reaction mixture as a crystalline solid employing conventional procedures.

The starting material represented by formula II may be prepared by the reaction of an appropriately substituted benzaldehyde compound, appropriate amino crotonic acid ester and appropriate acetoacetic ester as subsequently described.

The cyclization reaction to produce the cyclized products IA and IB may be carried out in the presence of an acid, including a Lewis acid. Suitable acids are gaseous hydrogen chloride and hydrogen bromide, and Lewis acids such as zinc iodide, zinc chloride, trimethylsilyl triflate, aluminum chloride, boron trifluoride, titanium tetrachloride and the like. Preferred as acids are gaseous hydrogen chloride and gaseous hydrogen bromide.

The reaction is carried out in an inert solvent as reaction medium. Suitable solvents include halogenated hydrocarbons such as methylene dichloride, ethylene dichloride, chloroform, carbon tetrachloride and the like.

The reaction is reasonably rapid taking place substantially immediately on the addition of the acid catalyst.

In carrying out the reaction according to the preferred method, gaseous hydrogen chloride is bubbled through a solution of II in an inert solvent for from a few minutes to several hours depending on the size of the operation. Then, after completion of the introduction of hydrogen chloride gas, the reaction mixture is stirred for several hours to complete the cyclization with the formation of the cyclized products as a tautomeric mixture. It has been found that the tautomers are not readily separable. The cyclized products may be recovered as a mixture from the reaction mixture by conventional procedures. Thus, the mixture may be neutralized with sodium bicarbonate solution, then diluted with water, extracted with water-immiscible organic solvent and recovered from the organic solution in the usual way.

The usefulness of the compounds of the present invention as calcium entry blockers may be demonstrated by the ability of the compounds to inhibit contraction of tracheal smooth muscle or of vascular tissue. The property may be observed in a test in which segments of vascular smooth muscle obtained from male Sprague-Dawley rats are suspended in physiological salt solution in a tissue bath instrumented for recording contractions. After the tissue has been equilibrated, washed in calcium-free physiological salt solution and then depolarized, 1.0 mM calcium chloride is re-added to induce contraction. After the contraction has reached a plateau, tissues are washed and a test compound or vehicle is added to determine the effect on a second contraction achieved by the above cyclic protocol. From measuring the initial contraction as well as the second contraction in the presence of the test compound, the extent of inhibition may be calculated.

When the 3:1 crystalline mixture of dimethyl 3,4a,5,6,10b-pentahydro-5-methoxy-2-methyl-4-methylidenebenzo (f)isoquinoline-1,4a-dicarboxylate and dimethyl 4a,5,6,10b-tetrahydro-5-methoxy-2,4-dimethylbenzo (f)isoquinoline-1,4a-dicarboxylate as representative of the compounds of the present invention was employed in the test, good inhibition of contraction of vascular smooth muscle from rat aorta was obtained at $10^{-5}$M.

For use in the chemotherapeutic treatment of cardiovascular diseases, an effective amount of the compounds of the present invention may be administered orally, parenterally, by inhalation, or by suppository, and in any suitable dosage form. For oral administration, the compounds may be offered in the form of tablets or capsules with suitable dispersants and carrier materials or dispersed in a liquid carrier for administration as solution or aqueous dispersion or emulsion; for parenteral administration, the compounds may be dispersed in an appropriate liquid carrier with or without dispersing agents depending on whether a solution, emulsion or other dispersion is intended; for aerosol administration the compound may be dispersed formulated with a suitable dispersant and propellant; and for use as suppository the compounds may be dispersed in a suitable carrier. Suitable carriers and dispersants are hereinafter described.

The ratio of the compound of the present invention to carrier varies with the particular compound, purpose and the mode of administration. The dosage level for the compounds may be varied from about 0.03 milligram to about 10 milligrams per kilogram of body weight per day. Daily doses in the range of 1 to 10 mg/kg are preferred. These doses are suitable for any of the methods of administration described herein.

To prepare the pharmaceutical compositions of this invention, the compounds of the present invention are intimately admixed with a pharmaceutical carrier according to conventional pharmaceutical compounding techniques, which carrier may take a wide variety of forms depending on the form of preparation desired for administration, e.g., oral or parenteral.

In preparing the compositions in oral dosage form, any of the usual pharmaceutical media may be employed. Thus, for liquid oral preparations, such as, for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques.

For parenterals, the carrier will usually comprise sterile water, although other ingredients may be included, for purposes such as, for example, for aiding solubility or for preservation. Injectable suspensions also may be prepared, in which case appropriate liquid carriers, suspending agents and the like may be employed.

The pharmaceutical compositions herein will contain, per dosage unit, e.g., tablet, capsule, powder, injection, teaspoonful and the like, from about 10 to about 500 mg of the active ingredient, preferably, from about 10 to about 250 mg.

The following examples illustrate the invention but are not to be construed as limiting.

EXAMPLE I

Dimethyl 3,4a,5,6,10b-pentahydro-5-methoxy-2-methyl-4-methylidenebenzo (f)isoquinoline-1,4a-dicarboxylate and Dimethyl 4a,5,6,10b-tetrahydro-5-methoxy-2,4-dimethylbenzo (f)isoquinoline-1,4a-dicarboxylate

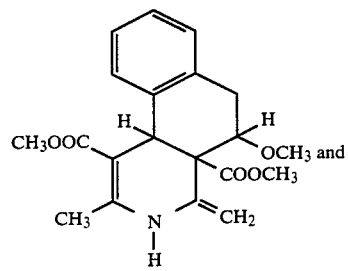

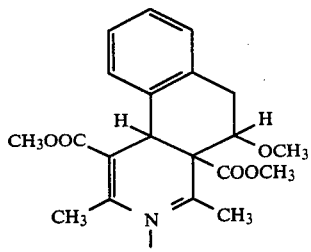

2-(2-Bromophenyl)ethanol

To a cooled to 0° C. solution of 10.0 grams (0.0465 mole) of 2-bromophenylacetic acid in 75 milliliters of dry tetrahydrofuran was added dropwise over a one-half hour period, a solution of 0.070 mole of borane in tetrahydrofuran while the reaction mixture was maintained under a nitrogen atmosphere. After completion of the addition, stirring was continued for one hour at ambient temperature, then cooled and the reaction quenched by adding 100 milliliters of water dropwise to the cooled mixture. Thereafter, the mixture was diluted with 100 milliliters of diethyl ether, sodium chloride was added to the resulting mixture and the organic and aqueous phases were mechanically separated. The organic solution was washed with saturated sodium bicarbonate solution and dried over sodium sulfate to obtain a clear, colorless dried solution. The solution was placed on a rotary evaporator to remove the solvent and to obtain 9.11 grams (98 percent) of the desired 2-(2-bromophenyl)ethanol intermediate as a clear oil. The $R_f$ was 0.5 on silica gel when eluted with one percent methanol in chloroform.

2-(2-Bromophenyl)acetaldehyde

A solution of 9.11 grams (0.045 mole) of 2-(2-bromophenyl)ethanol in 35 milliliters of methylene chloride was added to a stirred suspension of 14.62 grams (0.063 mole) of pyridinium chlorochromate in 75 milliliters of methylene chloride at ambient temperature whereupon a slightly exothermic reaction took place with the formation of a black reaction mixture. Stirring was continued for 15 hours at ambient temperature; then 150 milliliters of ether was added and the mixture filtered through silica gel on a pad of celite. The insoluble residue was washed with 100 milliliters of ether, filtered, the ether solutions combined and the solvents evaporated on a rotary evaporator to recover as residue, 8.0 grams (90 percent) of the desired 2-(2-bromophenyl)acetaldehyde intermediate as an oil. The oil had an $R_f$ of 0.6 on silica gel when eluted with one percent methanol in chloroform.

2-(2-Bromophenyl)acetaldehyde dimethylacetal

To a solution of 10.0 grams (0.05 mole) of 2-(2-bromophenyl)acetaldehyde (from the above preparation and another similar preparation) in 50 milliliters of dry methanol, was added 50 milliliters of trimethyl orthoformate and 0.25 gram of p-toluenesulfonic acid monohydrate and the resulting mixture was heated at reflux temperature for 3.5 hours. At the end of this period, the reaction mixture was cooled and 100 milliliters of diethyl ether and 50 milliliters of a 1:1 solution of 50 percent aqueous sodium hydroxide/brine were added. The ether solution was mechanically separated, washed, dried and stripped on the rotary evaporator to obtain 2-(2-bromophenyl)acetaldehyde dimethylacetal intermediate as a yellow oil. The latter was distilled to obtain 10.5 grams (85 percent yield) of purified product as a clear oil, b.p. 65°–67° /0.2 mm.

2-(2,2-Dimethoxyethyl)benzaldehyde

A hexane solution of 0.0041 mole of n-butyllithium was added dropwise to a cooled (−78° C.) solution of 1.0 gram (0.0041 mole) of 2-(2-bromophenyl)acetaldehyde dimethylacetal in 25 milliliters of tetrahydrofuran under an atmosphere of nitrogen at a rate such that the temperature within the reaction mixture was kept below −70° C. The resulting yellowish-brown suspension was stirred at −78° C. for 1 hour, then a solution of 0.46 gram (0.0041 mole) of N-formylpiperidine in 5 milliliters of tetrahydrofuran was added dropwise thereto. After completion of the addition, the solution was allowed to warm to room temperature over a period of about 12 hours to complete the reaction with the formation of 2-(2,2-dimethoxyethyl)benzaldehyde intermediate product in the reaction mixture. The mixture was then cooled and quenched with 20 milliliters of saturated ammonium chloride solution. Then, 30 milliliters of ether was added to extract the product and the ether solution washed with sodium bicarbonate solution, dried and stripped on a rotary evaporator to recover 0.40 gram (51 percent) of the desired 2-(2,2-dimethoxyethyl)benzaldehyde intermediate as a clear oil having $R_f$ of 0.6 on silica gel when eluted with 1:1 hexane/ether.

Dimethyl 2,6-dimethyl-4-[2-(2,2-dimethoxyethyl)phenyl]-1,4-dihydropyridine-3,5-dicarboxylate To a solution of 2.5 grams (0.013 mole) of 2-(2,2-dimethoxyethyl)benzaldehyde in 25 milliliters of dry methanol was added 1.48 grams (0.013 mole) of methyl 3-aminocrotonate and 1.49 grams (0.013 mole) of methyl acetoacetate and the resulting mixture was heated at reflux temperature for 3 days. At the end of this time, the solvent was removed on the rotary evaporator and the residue purified by flash chromatography on silica gel (250-400 mesh) using 2 percent methanol in chloroform as eluant to obtain 2.11 grams (42 percent yield) dimethyl 2,6-dimethyl-4-[2-(2,2-dimethoxyethyl)-phenyl]-1,4-dihydropyridine-3,5-dicarboxylate intermediate (R$_f$0.3) as a white solid, m.p. 113°-114° C.

Mixture of dimethyl
3,4a,5,6,10b-pentahydro-5-methoxy
-2-methyl-4-methylidenebenzo(f)isoquinoline-1,4a
-dicarboxylate and dimethyl
4a,5,6,10b-tetrahydro-5-methoxy
-2,4-dimethylbenzo(f)isoquinoline-1,4a-dicarboxylate Gaseous hydrogen chloride was bubbled into a solution of 0.78 gram (2 millimoles) of dimethyl 2,6-dimethyl-4-[2-(2,2-dimethoxyethyl) phenyl]-1,4-dihydropyridine-3,5-dicarboxylate in 20 milliliters of methylene chloride with stirring for twenty minutes. Thereafter, the mixture was stirred for an additional two hours to complete the cyclization. At the end of this time, the reaction mixture was neutralized with saturated sodium bicarbonate solution, diluted with 30 milliliters of water and the resulting solution extracted with two 50 milliliters portions of methylene chloride. The organic solutions were combined and washed with brine, dried, and the solvent vaporized to obtain 0.87 gram of a glassy solid. The solid was dissolved in 5 milliliters of ether and allowed to stand overnight to obtain 0.43 gram (60 percent yield) of crystalline material which discolored on standing. Hot cyclohexane was added to dissolve therein the crystalline material, and then cooled and filtered to remove insoluble impurities. The filtrate was concentrated to dryness and the residue obtained was dissolved in ether. The ethereal solution was allowed to stand whereupon crystals formed. The crystals had a melting point of 178°-80° C. and was determined by NMR analysis to be a 3:1 mixture of 3,4a,5,6,10b-pentahydro-5-methoxy-2-methyl-4-methyl- idenebenzo(f-)isoquinoline-1,4a-dicarboxylate and dimethyl 4a,5,6,10b-tetrahydro-5-methoxy-2,4-dimethylbenzo (f)isoquinoline-1,4a-dicarboxylate intermediate products.

EXAMPLE II

Dimethyl
3,4a,5,6,10b-pentahydro-8-bromo-5-methoxy-2-methyl
-4-methylidenebenzo(f)isoquinoline-1,4a-dicarboxylate
and Dimethyl 4a,5,6,10b-tetrahydro-5-methoxy
-2,4-dimethylbenzo(f)isoquinoline-1,4a-dicarboxylate

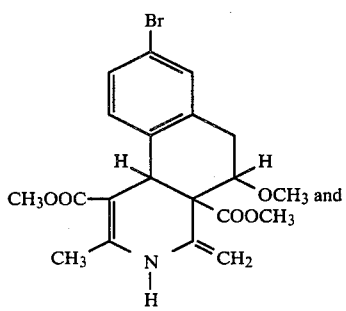

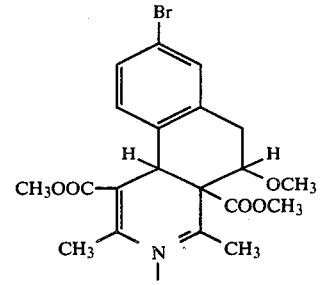

In a manner similar to that described in Example I, gaseous hydrogen chloride is bubbled into a solution of 0.87 gram (2 millimoles) of dimethyl 2,6-dimethyl-4-[2-(2,2-dimethoxyethyl)-4-bromophenyl]-1,4-dihydropyridine-3,5-dicarboxylate in 20 milliliters of methylene chloride with stirring and the stirring continued for several hours. Thereafter, the reaction mixture is neutralized with saturated sodium bicarbonate solution, diluted with water and then extracted twice with methylene chloride. The organic solutions are combined, washed, dried and the solvent vaporized to obtain a mixture of dimethyl 3,4a,5,6,10b-pentahydro-8-bromo-5-methoxy-2-methyl-4-methylidenebenzo (f)isoquinoline-1,4a-dicarboxylate and dimethyl 4a,5,6,10b-tetrahydro-8-bromo-5-methoxy-2,4-dimethylbenzo(f)isoquinoline-1,4a-dicarboxylate products.

EXAMPLE III

Diethyl
3,4a,5,6,10b-pentahydro-5-methoxy-2-methyl-4-
methylidene -9-nitro-benzo (f)isoquinoline
-1,4a-dicarboxylate and Diethyl 4a,5,6,10b-tetrahydro
-5-methoxy-2,4-dimethyl-9-nitrobenzo(f)isoquinoline
-1,4a-dicarboxylate

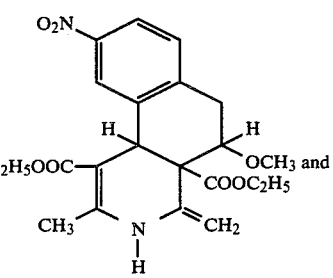

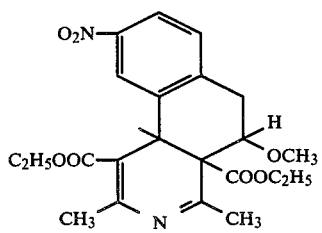

In a manner similar to that described in the preceding examples, gaseous hydrogen chloride is bubbled into a solution of 0.81 gram (2 millimoles) of diethyl 2,6-dimethyl-4-[2-(2,2-dimethoxyethyl-5-nitrophenyl]-1,4-dihydropyridine-3,5-dicarboxylate in 20 milliliters of methylene chloride with stirring and the stirring continued for several hours. At the end of this period the reaction mixture is neutralized with saturated sodium bicarbonate solution, diluted with water and extracted with methylene chloride to obtain a mixture of diethyl 3,4a,5,6,10b-pentahydro-5-methoxy -2-methyl-4-methylidene-9-nitro-benzo(f) isoquinoline-1,4a-dicarboxylate and diethyl 4a5,6,10b-tetrahydro -5-methoxy-2,4-dimethyl-9-nitro-benzo(f) isoquinoline-1,4a-dicarboxylate products.

EXAMPLE IV

In operations carried out as described in the preceding examples, mixture of compounds having the substituents indicated in the following table may be prepared:

| Compound | R | R' | X |
|----------|---|----|----|
| IVa | Et | Et | Et |
| IVb | Et | Et | Me |
| IVc | n-Bu | Et | $NO_2$ |
| IVd | n-$C_6H_{13}$ | Et | Cl |
| IVe | n-$C_6H_{13}$ | Et | $CH_3O$ |
| IVf | n-$C_6H_{13}$ | Me | MeO |
| IVg | Me | Me | iPr |
| IVh | Me | nPr | EtO |

EXAMPLE V 5000 compressed tablets, each containing as active ingredient 10 milligrams of the crystalline 3:1 mixture of dimethyl 3,4a,5,6,10b-pentahydro-5-methoxy -2-methyl-4-methylidenebenzo(f)isoquinoline1,4a -dicarboxylate and dimethyl 4a,5,6,10b-tetrahydro-5-methoxy-2,4-dimethylbenzo(f)isoquinoline-1,4a-dicarboxylate, are prepared from the following formulation:

|  | Grams |
|---|---|
| Active ingredient | 50 |
| Starch | 70 |
| Dibasic calcium phosphate hydrous | 500 |
| Calcium stearate | 2.5 |

The ingredients are finely powdered, mixed well, and then granulated with 10 percent starch paste. The granulation is dried and compressed into tablets using starch as a disintegrant and calcium stearate as lubricant.

EXAMPLE VI 10,000 hard gelatin capsules, each containing 25 milligrams of a crystalline mixture of dimethyl 3,4a,5,6,10b-pentahydro-5-methoxy-2-methyl-4-methylidenebenzo (f)isoquinoline-1,4a-dicarboxylate and dimethyl 4a,5,6,10b-tetrahydro-5-methoxy-2,4-dimethyl-benzo (f)isoquinoline-1,4a-dicarboxylate, are prepared from the following formulation:

|  | Grams |
|---|---|
| Active ingredient | 250 |
| Lactose | 750 |
| Starch | 250 |
| Talc | 250 |
| Calcium stearate | 10 |

A uniform mixture of the active and supplementary ingredients is prepared and filled into two-piece hard gelatin capsules. The capsules are suitable for oral administration to provide therapeutic relief for patients with cardiovascular disorders by alleviating cardiac arrhythmias and/or peripheral vasoconstriction.

PREPARATION OF THE STARTING MATERIALS

The starting dihydropyridine compound for preparing the compounds of the present invention may be prepared employing the reaction sequence seen in the following flow diagram or through a portion thereof depending on the availability of the precursor compounds:

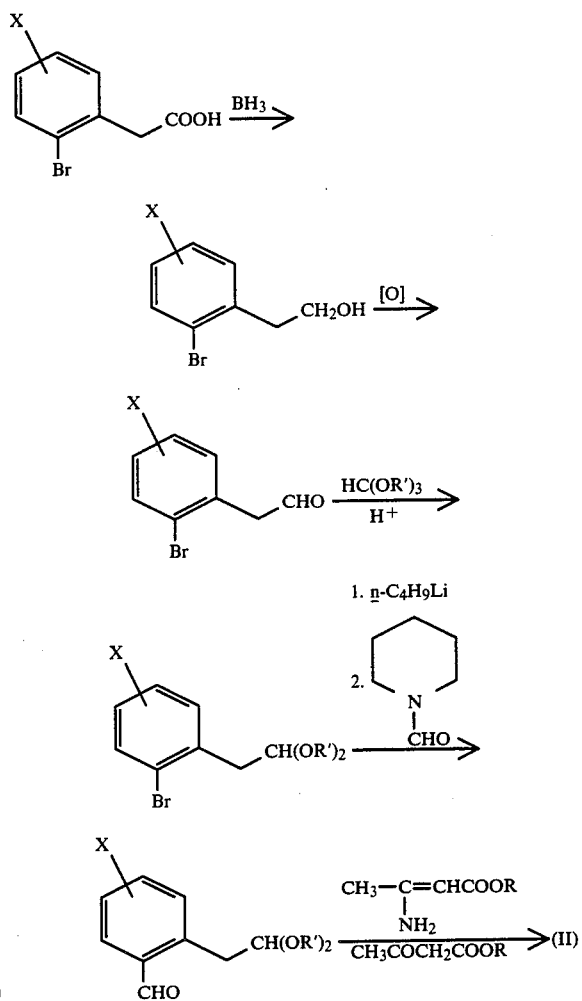

In carrying out the first step of the reaction, a solution of borane in tetrahydroruran is added dropwise with cooling in an atmosphere of nitrogen to a cooled, stirred solution of a 2-bromophenylacetic acid compound. After completion of the addition, stirring is continued with the formation of a 2-(2-bromophenyl)ethanol compound which may then be recovered by conventional procedures. (Although the nomenclature herein employed is consistent with X=H, the procedure is applicable to compounds in which X is other than H).

The oxidation of the 2-(2-bromophenyl)ethanol compound may be carried out by adding at ambient temperature, a halohydrocarbon solution thereof to a stirred suspension of pyridinium chlorochromate in a halohydrocarbon solvent for time sufficient to complete the reaction with the formation of the desired 2-(2-bromophenyl)acetaldehyde intermediate compound. The latter may be recovered from the reaction mixture by adding ether to the reaction mixture filtering off the spent oxidizing agent, and evaporating the solvent to obtain the aldehyde intermediate as an oil.

To a solution in dry methanol of the aldehyde compound thus obtained, is added an appropriate trialkyl orthoformate and p-toluenesulfonic acid, and the resulting mixture heated at reflux temperature for several hours. At the end of this time, the reaction mixture is cooled and diluted with diethyl ether. The resulting two-phase mixture is washed with 1:1 aqueous sodium hydroxide/brine, and the organic phase is separated and dried. The solvent then is evaporated from the dried solution to obtain the desired 2-(2-bromophenyl)acetaldehyde dialkylacetal intermediate as residue. The intermediate product may be purified by distilling.

The acetal compound may be converted to the desired benzaldehyde compound by first intimately mixing the acetal compound with a metal alkyl such as n-butyllithium at very low temperatures (less than −70° C.) in an atmosphere of nitrogen to obtain a metal derivative. Thereafter, a solution of N-formylpiperidine in an inert solvent such as tetrahydrofuran is added in a dropwise manner to the suspension of the metal derivative obtain a 2-(2,2-dimethoxyethyl) benzaldehyde compound. The reaction is then quenched with saturated ammonium chloride to remove the acetal alkoxy group and to obtain the desired benzaldehyde compound which then is recovered by extraction with ether followed by evaporation of the solvent.

The benzaldehyde compound thus obtained is dissolved in dry methanol and reacted with alkyl 3-aminocrotonate and alkyl acetoacetate by heating together at reflux temperature for time sufficient to complete the reaction with the formation of the 1,4-dihydropyridine compound of Formula II which may be obtained by vaporizing off the solvent and purifying by conventional procedures.

What is claimed is:

1. A composition comprising a crystalline mixture of compounds having the formulas:

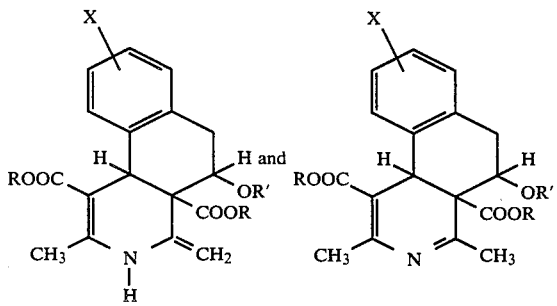

wherein R is lower alkyl; R' is lower alkyl; X is hydrogen, lower alkyl, lower alkoxy, nitro, trifluoromethyl or halogen.

2. A composition according to claim 1, wherein X is hydrogen.

3. A composition according to claim 1 wherein R is methyl.

4. A composition according to claim 1 wherein R' is methyl.

5. A composition according to claim 1 which is a mixture of dimethyl 3,4a,5,6,10b-pentahydro-5-methoxy-2-methyl-4-methylidenebenzo(f)isoquinoline dicarboxylate and dimethyl 4a,5,6,10b-tetrahydro-5-methoxy-2,4-dimethylbenzo(f)isoquinoline-1,4a-dicarboxylate.

6. A composition according to claim 5 in which the ratio of dimethyl 3,4a, 5,6,10b pentahydro-5-methoxy-2-methyl-4-methylidenebenzo(f)isoquinoline dicarboxylate and dimethyl 4a, 5, 6, 10b-tetrahydro-5-methoxy-2,4-dimethylbenzo(f)isoquinoline-1,4a-dicarboxylate is 3:1.

7. A pharmaceutical composition useful for the treatment of cardiovascular disorders caused by high cellular concentration of calcium comprising a therapeutically effective amount of a mixture of compounds having the formulas:

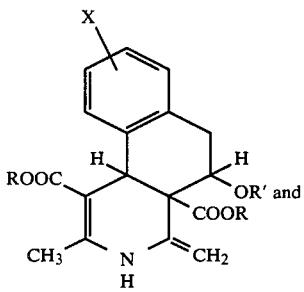

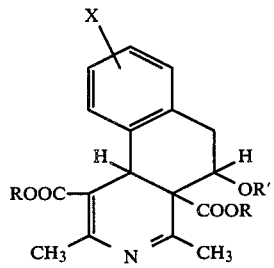

wherein R is lower alkyl; R' is lower alkyl; and X is hydrogen, lower alkyl, lower alkoxy, halogen or nitro, in admixture with a pharmaceutically acceptable carrier.

8. A method of treating cardiovascular disorders caused by high cellular concentration of calcium which comprises administering, to a person in need of treatment, a therapeutically effective amount of a composition of claim 1.

* * * * *